US009561309B2

(12) United States Patent
Glauser et al.

(10) Patent No.: US 9,561,309 B2
(45) Date of Patent: *Feb. 7, 2017

(54) ANTIFOULING HEPARIN COATINGS

(75) Inventors: Thierry Glauser, Redwood City, CA (US); Eugene Michal, San Francisco, CA (US); Charles Claude, Sunnyvale, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1751 days.

This patent is subject to a terminal disclaimer.

(21) Appl. No.: 10/857,141

(22) Filed: May 27, 2004

(65) Prior Publication Data

US 2005/0266038 A1 Dec. 1, 2005

(51) Int. Cl.
*A61L 31/10* (2006.01)
*C08L 33/14* (2006.01)
*A61L 31/16* (2006.01)
*C08L 1/00* (2006.01)

(52) U.S. Cl.
CPC ............... *A61L 31/10* (2013.01); *A61L 31/16* (2013.01); *C08L 33/14* (2013.01); *A61L 2300/416* (2013.01); *A61L 2300/42* (2013.01); *C08L 1/00* (2013.01)

(58) Field of Classification Search
None
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,688,317 A | 9/1972 | Kurtz | |
| 3,773,737 A | 11/1973 | Goodman et al. | 260/78 |
| 3,849,514 A | 11/1974 | Gray, Jr. et al. | 260/857 |
| 3,914,802 A | 10/1975 | Reick | |
| 4,226,243 A | 10/1980 | Shalaby et al. | 128/335.5 |
| 4,314,043 A * | 2/1982 | Kojima et al. | 525/102 |
| 4,329,383 A | 5/1982 | Joh | 428/36 |
| 4,331,697 A | 5/1982 | Kudo et al. | |
| 4,343,931 A | 8/1982 | Barrows | 528/291 |
| 4,420,395 A | 12/1983 | Tanihara et al. | |
| 4,478,961 A | 10/1984 | Tanaka et al. | |
| 4,510,135 A | 4/1985 | Teng | |
| 4,521,564 A | 6/1985 | Solomon et al. | |
| 4,529,792 A | 7/1985 | Barrows | 528/291 |
| 4,611,051 A | 9/1986 | Hayes et al. | 528/295.3 |
| 4,654,327 A | 3/1987 | Teng | |
| 4,656,242 A | 4/1987 | Swan et al. | 528/295.3 |
| 4,703,042 A | 10/1987 | Bodor | |
| 4,733,665 A | 3/1988 | Palmaz | 128/343 |
| 4,745,180 A | 5/1988 | Moreland et al. | |
| 4,800,882 A | 1/1989 | Gianturco | 128/343 |
| 4,834,746 A | 5/1989 | Kira | |
| 4,871,357 A | 10/1989 | Hsu et al. | |
| 4,882,168 A | 11/1989 | Casey et al. | 424/468 |
| 4,886,062 A | 12/1989 | Wiktor | 128/343 |
| 4,931,287 A | 6/1990 | Bae et al. | 424/484 |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | 623/1 |
| 5,047,020 A | 9/1991 | Hsu | |
| 5,069,899 A * | 12/1991 | Whitbourne et al. | 424/56 |
| 5,081,161 A * | 1/1992 | Ostapchenko | A61L 27/56 428/36.5 |
| 5,084,065 A | 1/1992 | Weldon et al. | |
| 5,092,841 A | 3/1992 | Spears | |
| 5,100,992 A | 3/1992 | Cohn et al. | 424/501 |
| 5,112,457 A | 5/1992 | Marchant | 204/165 |
| 5,133,742 A | 7/1992 | Pinchuk | 623/1 |
| 5,141,991 A * | 8/1992 | Konno et al. | 525/102 |
| 5,151,192 A | 9/1992 | Matkovich et al. | |
| 5,163,952 A | 11/1992 | Froix | 623/1 |
| 5,165,919 A | 11/1992 | Sasaki et al. | 424/488 |
| 5,204,323 A | 4/1993 | Findlay et al. | |

(Continued)

FOREIGN PATENT DOCUMENTS

| | | |
|---|---|---|
| DE | 42 24 401 | 1/1994 |
| EP | 0 301 856 | 2/1989 |
| EP | 0 396 429 | 11/1990 |
| EP | 0 514 406 | 11/1992 |
| EP | 0 596 615 | 5/1994 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |

(Continued)

OTHER PUBLICATIONS

Byun et al. Journal of Biomedical Materials Research 1996 30:423-427.*
Kang et al. Journal of Biomaterials Science, Polymer Edition 2001 12:1091-1108.*
Shoichet et al. Macromolecules 1991 24:982-986.*

(Continued)

*Primary Examiner* — Robert A Wax
*Assistant Examiner* — Caralynne Helm
(74) *Attorney, Agent, or Firm* — Squire Patton Boggs (US) LLP

(57) ABSTRACT

A medical device comprising a coating thereon comprising a biocompatible polymer and heparin is provided herein. Heparin is coupled with the biocompatible polymer via a spacer having a grouping that renders a binding site of the heparin molecule accessible by a binding protein. The medical device can be implanted in a human being for the treatment of a disease such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

23 Claims, 1 Drawing Sheet

(56) References Cited

U.S. PATENT DOCUMENTS

| | | | |
|---|---|---|---|
| 5,217,492 A * | 6/1993 | Guire | A61F 2/0077 427/2.24 |
| 5,219,980 A | 6/1993 | Swidler | 528/272 |
| 5,232,444 A | 8/1993 | Just et al. | |
| 5,236,570 A | 8/1993 | Ma et al. | |
| 5,258,020 A | 11/1993 | Froix | 623/1 |
| 5,270,046 A | 12/1993 | Sakamoto et al. | |
| 5,272,012 A | 12/1993 | Opolski | |
| 5,276,015 A | 1/1994 | Khouri et al. | |
| 5,292,516 A | 3/1994 | Viegas et al. | 424/423 |
| 5,296,471 A | 3/1994 | Holme et al. | |
| 5,298,260 A | 3/1994 | Viegas et al. | 424/486 |
| 5,300,295 A | 4/1994 | Viegas et al. | 424/427 |
| 5,302,385 A | 4/1994 | Khan et al. | |
| 5,304,121 A | 4/1994 | Sahatjian | |
| 5,306,501 A | 4/1994 | Viegas et al. | 424/423 |
| 5,306,786 A | 4/1994 | Moens et al. | 525/437 |
| 5,328,471 A | 7/1994 | Slepian | 604/101 |
| 5,330,768 A | 7/1994 | Park et al. | 424/501 |
| 5,350,800 A | 9/1994 | Verhoeven et al. | |
| 5,356,433 A | 10/1994 | Rowland et al. | |
| 5,372,719 A | 12/1994 | Afeyan et al. | |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,453,171 A | 9/1995 | Ma et al. | |
| 5,455,040 A | 10/1995 | Marchant | |
| 5,457,158 A * | 10/1995 | Caporiccio et al. | 525/102 |
| 5,462,990 A | 10/1995 | Hubbell et al. | 525/54.1 |
| 5,464,650 A | 11/1995 | Berg et al. | |
| 5,475,052 A | 12/1995 | Rhee et al. | |
| 5,476,909 A * | 12/1995 | Kim et al. | 525/408 |
| 5,480,436 A * | 1/1996 | Bakker et al. | 600/37 |
| 5,485,496 A | 1/1996 | Lee et al. | 378/64 |
| 5,496,346 A | 3/1996 | Horzewski et al. | |
| 5,507,768 A | 4/1996 | Lau et al. | |
| 5,516,881 A | 5/1996 | Lee et al. | 528/320 |
| 5,545,213 A | 8/1996 | Keogh et al. | |
| 5,554,689 A * | 9/1996 | Langstein et al. | 525/102 |
| 5,569,463 A | 10/1996 | Helmus et al. | 424/426 |
| 5,575,818 A | 11/1996 | Pinchuk et al. | |
| 5,578,073 A | 11/1996 | Haimovich et al. | 623/1 |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,609,629 A | 3/1997 | Fearnot et al. | 623/1 |
| 5,610,241 A | 3/1997 | Lee et al. | 525/411 |
| 5,616,338 A | 4/1997 | Fox, Jr. et al. | 424/423 |
| 5,618,298 A | 4/1997 | Simon | |
| 5,624,411 A | 4/1997 | Tuch | 604/265 |
| 5,628,730 A | 5/1997 | Shapland et al. | 604/21 |
| 5,644,020 A | 7/1997 | Timmermann et al. | 528/288 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,696,100 A | 12/1997 | Holme et al. | |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,728,751 A * | 3/1998 | Patnaik | 523/112 |
| 5,735,897 A | 4/1998 | Buirge | 623/12 |
| 5,741,881 A | 4/1998 | Patnaik | |
| 5,746,998 A | 5/1998 | Torchilin et al. | 424/9.4 |
| 5,759,205 A | 6/1998 | Valentini | 623/16 |
| 5,770,563 A | 6/1998 | Roberts et al. | |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,808,021 A | 9/1998 | Holme et al. | |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,836,962 A | 11/1998 | Gianotti | |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,854,376 A | 12/1998 | Higashi | 528/288 |
| 5,855,618 A | 1/1999 | Patnaik et al. | |
| 5,858,746 A | 1/1999 | Hubbell et al. | 435/177 |
| 5,858,990 A | 1/1999 | Walsh | |
| 5,865,723 A | 2/1999 | Love | |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | |
| 5,876,463 A * | 3/1999 | Garcia | A61K 8/85 8/405 |
| 5,877,224 A | 3/1999 | Brocchini et al. | 514/772.2 |
| 5,879,713 A | 3/1999 | Roth et al. | 424/489 |
| 5,897,955 A | 4/1999 | Drumheller | |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,549 A | 4/2000 | Roberts et al. | |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,096,525 A | 8/2000 | Patnaik | |
| 6,099,562 A | 8/2000 | Ding et al. | 623/1.46 |
| 6,107,416 A | 8/2000 | Patnaik et al. | |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | 604/502 |
| 6,120,536 A * | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,132,462 A | 10/2000 | Li | |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,193,746 B1 | 2/2001 | Strecker | |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,231,600 B1 | 5/2001 | Zhong | 623/1.42 |

(56) References Cited

U.S. PATENT DOCUMENTS

| | | |
|---|---|---|
| 6,240,616 B1 | 6/2001 | Yan .................. 29/527.2 |
| 6,245,753 B1 | 6/2001 | Byun et al. |
| 6,245,760 B1 | 6/2001 | He et al. ............. 514/234.8 |
| 6,248,129 B1 | 6/2001 | Froix .................. 623/1.42 |
| 6,251,136 B1 | 6/2001 | Guruwaiya et al. ...... 623/1.46 |
| 6,254,632 B1 | 7/2001 | Wu et al. ............. 623/1.15 |
| 6,258,121 B1 | 7/2001 | Yang et al. ........... 623/1.46 |
| 6,258,371 B1 | 7/2001 | Koulik et al. .......... 424/422 |
| 6,262,034 B1 | 7/2001 | Mathiowitz et al. ........ 514/44 |
| 6,270,788 B1 | 8/2001 | Koulik et al. |
| 6,273,913 B1 | 8/2001 | Wright et al. |
| 6,277,449 B1 | 8/2001 | Kolluri et al. ............. 427/289 |
| 6,283,947 B1 | 9/2001 | Mirzaee .................. 604/264 |
| 6,283,949 B1 | 9/2001 | Roorda ................ 604/288.02 |
| 6,284,305 B1 | 9/2001 | Ding et al. .............. 427/2.28 |
| 6,287,285 B1 | 9/2001 | Michal et al. |
| 6,287,628 B1 | 9/2001 | Hossainy et al. ............ 427/2.3 |
| 6,299,604 B1 | 10/2001 | Ragheb et al. ............ 604/265 |
| 6,306,176 B1 | 10/2001 | Whitbourne ............ 623/23.59 |
| 6,331,313 B1 | 12/2001 | Wong et al. ............. 424/427 |
| 6,335,029 B1 | 1/2002 | Kamath et al. ........... 424/423 |
| 6,338,904 B1 | 1/2002 | Patnaik et al. |
| 6,344,035 B1 | 2/2002 | Chudzik et al. .......... 604/265 |
| 6,346,110 B2 | 2/2002 | Wu ....................... 606/108 |
| 6,358,556 B1 | 3/2002 | Ding et al. ............. 427/2.24 |
| 6,361,819 B1 | 3/2002 | Tedeschi et al. |
| 6,369,168 B1 | 4/2002 | Al-Lamee et al. |
| 6,379,381 B1 | 4/2002 | Hossainy et al. ......... 623/1.42 |
| 6,383,215 B1 | 5/2002 | Sass |
| 6,387,379 B1 | 5/2002 | Goldberg et al. ......... 424/400 |
| 6,395,326 B1 | 5/2002 | Castro et al. ........... 427/2.24 |
| 6,419,692 B1 | 7/2002 | Yang et al. ............ 623/1.15 |
| 6,451,373 B1 | 9/2002 | Hossainy et al. ........ 427/2.25 |
| 6,458,383 B2 | 10/2002 | Chen et al. |
| 6,465,588 B1 | 10/2002 | Li |
| 6,482,834 B2 | 11/2002 | Spada et al. ............ 514/311 |
| 6,494,862 B1 | 12/2002 | Ray et al. ............ 604/96.01 |
| 6,497,729 B1 | 12/2002 | Moussy et al. |
| 6,503,538 B1 | 1/2003 | Chu et al. .............. 424/497 |
| 6,503,556 B2 | 1/2003 | Harish et al. .......... 427/2.24 |
| 6,503,954 B1 | 1/2003 | Bhat et al. ............ 514/772.2 |
| 6,506,437 B1 | 1/2003 | Harish et al. .......... 427/2.25 |
| 6,524,347 B1 | 2/2003 | Myers et al. |
| 6,525,145 B2* | 2/2003 | Gevaert et al. ........... 525/450 |
| 6,527,801 B1 | 3/2003 | Dutta .................... 623/1.46 |
| 6,527,863 B1 | 3/2003 | Pacetti et al. ............ 118/500 |
| 6,528,526 B1 | 3/2003 | Myers et al. ............. 214/311 |
| 6,530,950 B1 | 3/2003 | Alvarado et al. ......... 623/1.13 |
| 6,530,951 B1 | 3/2003 | Bates et al. ............ 623/1.45 |
| 6,540,776 B2 | 4/2003 | Sanders Millare et al. . 623/1.15 |
| 6,544,223 B1 | 4/2003 | Kokish ................ 604/103.01 |
| 6,544,543 B1 | 4/2003 | Mandrusov et al. ....... 424/422 |
| 6,544,582 B1 | 4/2003 | Yoe .................... 427/2.24 |
| 6,555,157 B1 | 4/2003 | Hossainy ............... 427/2.24 |
| 6,558,733 B1 | 5/2003 | Hossainy et al. ......... 427/2.24 |
| 6,565,659 B1 | 5/2003 | Pacetti et al. ............ 118/500 |
| 6,572,644 B1 | 6/2003 | Moein ................... 623/1.11 |
| 6,585,755 B2 | 7/2003 | Jackson et al. .......... 623/1.15 |
| 6,585,765 B1 | 7/2003 | Hossainy et al. ......... 623/1.45 |
| 6,585,926 B1 | 7/2003 | Mirzaee ................... 264/400 |
| 6,589,943 B2 | 7/2003 | Byun et al. |
| 6,605,154 B1 | 8/2003 | Villareal ................. 118/500 |
| 6,616,765 B1 | 9/2003 | Castro et al. ............ 623/1.45 |
| 6,623,448 B2 | 9/2003 | Slater .................. 604/95.01 |
| 6,625,486 B2 | 9/2003 | Lundkvist et al. .......... 604/21 |
| 6,630,580 B2 | 10/2003 | Tsang et al. |
| 6,645,135 B1 | 11/2003 | Bhat ..................... 600/3 |
| 6,645,195 B1 | 11/2003 | Bhat et al. .............. 604/528 |
| 6,656,216 B1 | 12/2003 | Hossainy et al. .......... 623/1.13 |
| 6,656,506 B1 | 12/2003 | Wu et al. ................ 424/489 |
| 6,660,034 B1 | 12/2003 | Mandrusov et al. ....... 623/1.42 |
| 6,663,662 B2 | 12/2003 | Pacetti et al. ............ 623/1.13 |
| 6,663,880 B1 | 12/2003 | Roorda et al. ............ 424/423 |
| 6,666,880 B1 | 12/2003 | Chiu et al. .............. 623/1.11 |
| 6,673,154 B1 | 1/2004 | Pacetti et al. ............ 118/500 |
| 6,673,385 B1 | 1/2004 | Ding et al. .............. 427/2.28 |
| 6,682,886 B1* | 1/2004 | Gold .................. C12Q 1/6811 |
| | | 435/6.16 |
| 6,689,099 B2 | 2/2004 | Mirzaee ................ 604/107 |
| 6,695,920 B1 | 2/2004 | Pacetti et al. ............ 118/500 |
| 6,706,013 B1 | 3/2004 | Bhat et al. ............. 604/96.01 |
| 6,706,289 B2* | 3/2004 | Lewis et al. ............. 424/501 |
| 6,709,514 B1 | 3/2004 | Hossainy ............... 118/52 |
| 6,712,845 B2 | 3/2004 | Hossainy ................ 623/1.42 |
| 6,713,119 B2 | 3/2004 | Hossainy et al. .......... 427/2.25 |
| 6,716,444 B1 | 4/2004 | Castro et al. ............ 424/422 |
| 6,723,120 B2 | 4/2004 | Yan ..................... 623/1.15 |
| 6,733,768 B2 | 5/2004 | Hossainy et al. .......... 424/426 |
| 6,740,040 B1 | 5/2004 | Mandrusov et al. ........ 600/439 |
| 6,743,462 B1 | 6/2004 | Pacetti ................. 427/2.24 |
| 6,749,626 B1 | 6/2004 | Bhat et al. .............. 623/1.1 |
| 6,753,071 B1 | 6/2004 | Pacetti ................. 428/212 |
| 6,758,859 B1 | 7/2004 | Dang et al. ............. 623/1.15 |
| 6,759,054 B2 | 7/2004 | Chen et al. .............. 424/423 |
| 6,764,505 B1 | 7/2004 | Hossainy et al. .......... 623/1.15 |
| 6,929,955 B2 | 8/2005 | Bucha et al. |
| 6,961,610 B2 | 11/2005 | Yang et al. |
| 7,077,860 B2 | 7/2006 | Yan et al. |
| 7,396,541 B2 | 7/2008 | Hossainy et al. |
| 7,494,824 B2 | 2/2009 | Bucha et al. |
| 7,722,894 B2 | 5/2010 | Wang et al. |
| 2001/0007083 A1 | 7/2001 | Roorda .................. 623/1.15 |
| 2001/0014717 A1 | 8/2001 | Hossainy et al. .......... 525/60 |
| 2001/0018469 A1 | 8/2001 | Chen et al. |
| 2001/0020011 A1 | 9/2001 | Mathiowitz et al. |
| 2001/0027340 A1 | 10/2001 | Wright et al. |
| 2001/0029351 A1 | 10/2001 | Falotico et al. |
| 2001/0037145 A1 | 11/2001 | Guruwaiya et al. ......... 623/1.15 |
| 2001/0044651 A1 | 11/2001 | Steinke et al. |
| 2001/0044654 A1 | 11/2001 | Chen et al. |
| 2001/0051608 A1 | 12/2001 | Mathiowitz et al. |
| 2002/0004101 A1 | 1/2002 | Ding et al. |
| 2002/0005206 A1 | 1/2002 | Falotico et al. ........... 128/898 |
| 2002/0007213 A1 | 1/2002 | Falotico et al. ........... 623/1.21 |
| 2002/0007214 A1 | 1/2002 | Falotico ................. 623/1.21 |
| 2002/0007215 A1 | 1/2002 | Falotico et al. ........... 623/1.21 |
| 2002/0009604 A1 | 1/2002 | Zamora et al. ............ 428/450 |
| 2002/0013549 A1* | 1/2002 | Zhong et al. ............. 604/104 |
| 2002/0016625 A1 | 2/2002 | Falotico et al. ........... 623/1.13 |
| 2002/0032414 A1 | 3/2002 | Ragheb et al. ............ 604/265 |
| 2002/0032434 A1 | 3/2002 | Chudzik et al. .......... 604/890.1 |
| 2002/0051730 A1 | 5/2002 | Bodnar et al. ............. 422/33 |
| 2002/0062148 A1 | 5/2002 | Hart |
| 2002/0071822 A1 | 6/2002 | Uhrich .................. 424/78.37 |
| 2002/0077693 A1 | 6/2002 | Barclay et al. ........... 623/1.13 |
| 2002/0082679 A1 | 6/2002 | Sirhan et al. ............ 623/1.15 |
| 2002/0087123 A1 | 7/2002 | Hossainy et al. ........... 604/198 |
| 2002/0091433 A1 | 7/2002 | Ding et al. |
| 2002/0094440 A1 | 7/2002 | Llanos et al. ............ 428/421 |
| 2002/0111590 A1 | 8/2002 | Davila et al. ............ 604/265 |
| 2002/0120326 A1 | 8/2002 | Michal ................. 623/1.15 |
| 2002/0123505 A1 | 9/2002 | Mollison et al. |
| 2002/0123801 A1 | 9/2002 | Pacetti et al. ............ 623/1.46 |
| 2002/0133183 A1* | 9/2002 | Lentz et al. ............. 606/155 |
| 2002/0142039 A1 | 10/2002 | Claude .................. 424/486 |
| 2002/0155212 A1 | 10/2002 | Hossainy ................ 427/2.25 |
| 2002/0165608 A1 | 11/2002 | Llanos et al. ............ 623/1.45 |
| 2002/0176849 A1 | 11/2002 | Slepian ................. 424/93.7 |
| 2002/0183581 A1 | 12/2002 | Yoe et al. ................ 600/3 |
| 2002/0188037 A1 | 12/2002 | Chudzik et al. ........... 523/112 |
| 2002/0188277 A1 | 12/2002 | Roorda et al. ............ 604/523 |
| 2002/0192449 A1* | 12/2002 | Hobbs et al. ............ 428/297.4 |
| 2002/0197261 A1* | 12/2002 | Li et al. ................ 424/178.1 |
| 2003/0004141 A1 | 1/2003 | Brown .................. 514/152 |
| 2003/0021762 A1 | 1/2003 | Luthra et al. |
| 2003/0028243 A1 | 2/2003 | Bates et al. |
| 2003/0028244 A1 | 2/2003 | Bates et al. |
| 2003/0031780 A1 | 2/2003 | Chudzik et al. .......... 427/2.1 |
| 2003/0032767 A1 | 2/2003 | Tada et al. ............. 528/310 |
| 2003/0036794 A1 | 2/2003 | Ragheb et al. |
| 2003/0039689 A1 | 2/2003 | Chen et al. .............. 424/468 |
| 2003/0040712 A1 | 2/2003 | Ray et al. .............. 604/173 |
| 2003/0040790 A1 | 2/2003 | Furst .................... 623/1.11 |
| 2003/0059520 A1 | 3/2003 | Chen et al. ............. 427/2.1 |

(56) References Cited

U.S. PATENT DOCUMENTS

| | | | |
|---|---|---|---|
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0138487 A1 | 7/2003 | Hogan et al. | |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0203991 A1* | 10/2003 | Schottman et al. | 523/334 |
| 2003/0207020 A1 | 11/2003 | Villareal | 427/2.24 |
| 2003/0211230 A1 | 11/2003 | Pacetti et al. | 427/2.24 |
| 2003/0236514 A1 | 12/2003 | Schwarz | |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096476 A1 | 5/2004 | Uhrich et al. | |
| 2004/0096504 A1 | 5/2004 | Michal | 424/471 |
| 2004/0098117 A1 | 5/2004 | Hossainy et al. | 623/1.42 |
| 2004/0180039 A1 | 9/2004 | Toner et al. | |
| 2005/0239131 A1 | 10/2005 | Bucha et al. | |
| 2006/0014720 A1 | 1/2006 | Hossainy et al. | |
| 2006/0121085 A1* | 6/2006 | Warren | A61K 9/0024 424/426 |
| 2006/0178738 A1 | 8/2006 | Yan et al. | |

FOREIGN PATENT DOCUMENTS

| | | |
|---|---|---|
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 947 205 | 10/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 06-218038 | 8/1994 |
| JP | 08-191887 | 7/1996 |
| JP | 2001-500407 | 1/2001 |
| JP | 2001-500408 | 1/2001 |
| JP | 2001-190687 | 7/2001 |
| JP | 2001-519839 | 10/2001 |
| JP | 2001-527539 | 12/2001 |
| JP | 2002-501788 | 1/2002 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 89/05616 | 6/1989 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/10805 | 3/1998 |
| WO | WO 98/10806 | 3/1998 |
| WO | WO 98/17331 | 4/1998 |
| WO | WO 98/32398 | 7/1998 |
| WO | WO 98/36784 | 8/1998 |
| WO | WO 98/46648 A1 | 10/1998 |
| WO | WO 98/49206 A1 | 11/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 0021572 A2 * | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/067908 | 9/2002 |
| WO | WO 02/085419 | 10/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/021976 | 3/2004 |
| WO | WO 2004/026359 | 4/2004 |

OTHER PUBLICATIONS

Betz et al. Nuclear Instruments and Methods in Physics Research B 2003 208:434-441.*

Na et al. Biotechnology Letters 2003 25:381-385.*

Manta et al. Enzyme and Microbial Technology 2003 33:890-898.*

Search Report and the Written Opinion for PCT/US2005/017811, filed May 19, 2005, mailed Aug. 10, 2005, 14 pgs.

Vulić et al., "Heparin-containing block copolymers. Part II *In vitro and ex vivo blood compatibility*", J. of Mat. Science Materials in Medicine vol. 4, No. 5, pp. 448-459, 1993.

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

(56) References Cited

OTHER PUBLICATIONS

Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis($\alpha$-amino acid)$\alpha,\omega$-Alkylene Diesters, and Aliphatic Dicarbolic Acids*, Journal of Polymer Science, Part A: Polymer Chemistry, 37(4), 391-407 (1999).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, European Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising $\alpha$-Amino Acid, 1,2-Ethanediol, and Adipic Acid*, Chemistry Letters, pp. 21-24, (1991).
Shigeno, *Prevention of Cerebrovascular Spasm by Bosentan, Novel Endothelin Receptor*, Chemical Abstract 125:212307 (1996).
van Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).
Soons et al., *The heparin-catalysed inhibition of human Factor XIa by antithrombin III is dependent on the heparin type*, Biochem.J. vol. 256, 815-820 (1988).
Luo et al., *Cross-linked hyaluronic acid hydrogel films: new biomaterials for drug delivery*, Journal of Controlled Release 69 (2000) 169-184.
Translation of Notification of Refusal received from JPO for Appl. No. 2007-515203, mailed Apr. 24, 2012, 7 pgs.
PartialTranslation of Notification of Refusal received from JPO for Appl. No. 2007-515203, mailed Feb. 5, 2013, 2 pgs.
CAS Registry file for Hyaluronic acid, accessed Oct. 9, 2008.
Devaux "Static and Dynamic Lipid Asymmetry in Cell Membranes", Biochemsitry 30(5), p. 1173-1179, (1991).
Galli et al. "Acute and Mid-Term Results of Phosphorylcholine-Coated Stents in Primary Coronary Stenting for Acute Myocardial Infarction" Catheterization and Cardiovascular Interventions 53, p. 182-187 (2001).
Luo et al., "Cross-linked hyaluronic acid hydrogel films: new biomaterials for drug delivery", J. of Controlled Release 69, pp. 169-184 (2000).
Medtronic, Trillium Affinity NT, Oxygenator, Product Information, 6 pages (2000).
Palanzo et al. "Effect of Carmeda®", Perfusion 16, pp. 279-283 (2001).
Simon et al. "Species Variations in Phospholipid Class Distribution of Organs II. Heart and Skeletal Muscle" Lipids 4(6), pp. 607-614 (1969).
Soons et al., "The heparin-catalysed inhibition of human Factor Xia by antithrombin III is dependent on the heparin type", Biochem J. 256, pp. 815-820 (1988).
Sun et al. "Synthesis and Terminal Functionalization of a Polymerizable Phosphatidylethanolamine", Biconjugate Chemistry, 12(5), pp. 673-677 (2001).
Trillium(R) Affinity(R) NT Oxygenator Product Monograph from Medtronic, 6 pgs. (2000).
U.S. Appl. No. 11/171,111, filed Jun. 29, 2005, Glauser et al.
Durrani et al. "Biomembranes as models for polymer surfaces," Biomaterials, vol. 7, 1996, pp. 121-125.
Francois et al. "Physical and biological effects of a surface coating procedure on polyurethane catheters," Biomaterials, vol. 17, No. 7, 1996, pp. 667-678.
Gautier et al. "Amphiphilic copolymers of $_\epsilon$-caprolactone and $_\gamma$-substituted $_\epsilon$-caprolactone. Synthesis and functionalization of poly(D,L-lactide) nanoparticles." J. Biomater. Sci. Polymer Edn, vol. 14, No. 1, 2003, pp. 63-85.
Gisselfat et al. "Effect of Sort Segment Length and Chain Extender Structure on Phase Separation and Morphology in Poly (urethane urea)s" Macromol. Mater. Eng., vol. 288, 2003, pp. 265-271.
Lamberg et al. "Glycosaminoglycans, A Biochemical and Clinical Review," J. Invest. Dermatol., vol. 63, No. 6, 1974, pp. 433-449.
Lee et al. "Synthesis and Degradation of End-Group-Functionalized Polylactide," Journal of Polymer Science: Part A: Polymer Chemistry, vol. 39, 2001, pp. 973-985.
Park et al. "Blood compatibility of SPUU-PEO-heparin graft copolymers," Journal of Biomedical Materials Research, vol. 26, 1992, pp. 739-756.

\* cited by examiner

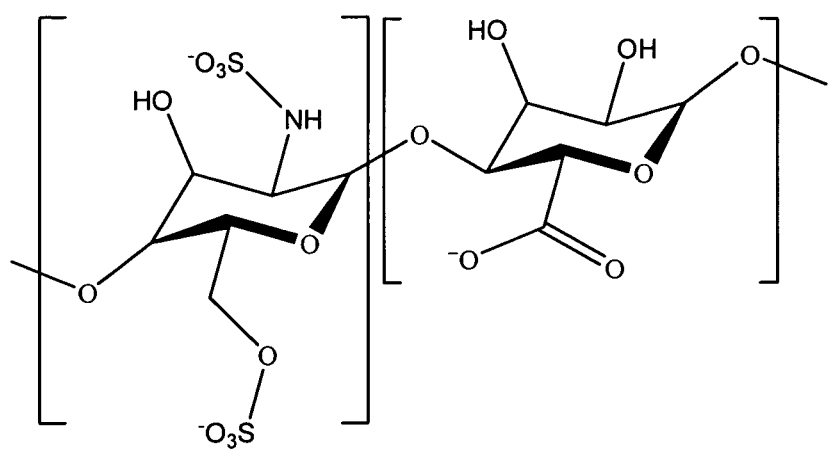

ANTIFOULING HEPARIN COATINGS

BACKGROUND OF THE INVENTION

Field of the Invention

This invention generally relates to a coating having heparin attached thereto on an implantable device, such as a stent.

Description of the Background

Blood has a property of being coagulated by the action of various components in blood when it has come into contact with foreign matters. Hence, there is need for a high anti-coagulant property in component materials for medical articles or instruments used on the part coming into contact with blood, as exemplified by artificial hearts, artificial cardiac valves, artificial blood vessel, blood vessel catheters cannulas, pump-oxygenators, blood vessel by-pass tubes, intraaortic balloon pumping, transfusion instruments and extracorporeal circulation circuits. Heparin has been commonly used to impart to the medical devices anticoagulant properties, but a systemic use of heparin may undesirably lead to the formation of a large number of bleeding nests.

Methods have been developed to minimize side effects associated with the use of heparin with limited success (see, for example, U.S. Pat. Nos. 5,270,064 and 6,630,580). The efficacy of using heparin not only depends on the nature and property of heparin, but also depends on the nature and property of the materials used in associated with heparin. For example, surfaces in-vivo are quickly covered by proteins, which may thus reduce the effectiveness of heparin attached thereto. Moreover, direct attachment of heparin to substrate surfaces may block the binding sites on the heparin molecule such that they become inaccessible to the binding proteins, further reducing the effectiveness of heparin.

The present invention addresses such problems by providing a coating composition for coating implantable devices.

SUMMARY OF THE INVENTION

Provided herein is heparin attached to a substrate surface via a spacer. The spacer is sufficiently long that allows the binding sites of the heparin molecule to be accessible to binding proteins. The substrate is optionally coated with an anti-fouling material. In one embodiment, the spacer is poly(ethylene glycol) (PEG) having a molecular weight of between, e.g., about 500 daltons to 5,000 daltons.

The substrate can be coated with any biocompatible polymeric material. The polymeric material can be hydrophilic or hydrophobic. Preferably, the polymeric material is a non-fouling material. In one embodiment, the anti-fouling material can be, for example, PEG, etc. The coating optionally includes an anti-fouling material. The coating may further include a bioactive agent.

BRIEF DESCRIPTION OF THE FIGURES

FIG. 1 shows heparin's building blocks: glycosamine and iduronic acid.

DETAILED DESCRIPTION

Provided herein is a coating formed of a biocompatible polymer having heparin attached thereto via a spacer. Heparin can be used as is or used in a modified form. The spacer comprises a grouping that renders the heparin molecule attached to the polymer to be flexible such that the binding sites of the heparin molecule become accessible by binding proteins. Particularly, the attached heparin molecule with a spacer and a binding protein bond to each other, as described in Scheme 1 below, with a binding constant ($K_d$) (Equation 1) of about 0.01 to 1 micromolar, for example, about 0.01 to 0.28 micromolars.

Scheme 1

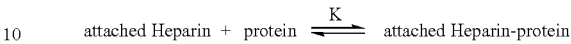

The heparin binding expression can be given by Equation 1:

$$K_d = [AT\text{-}III_f] \times [S_f]/[AT\text{-}III_b] \quad \text{(Equation 1)}$$

where $AT\text{-}III_f$ is the concentration of free antithrombin, $AT\text{-}III_b$ is the concentration of bound antithrombin, and $S_f$ is the concentration of free binding sites on the heparin (Soons H, Tans G. Hemker HC, Biochem. J. (1988): 256 (815-820).

The coating optionally includes an anti-fouling or non-fouling material. The coating may further include a bioactive agent. As used herein, the term anti-fouling and non-fouling are used interchangeably. Non-fouling or anti-fouling is defined as preventing, delaying or reducing the amount of formation of protein build-up caused by the body's reaction to foreign material.

Heparin

Heparin is a highly charged glycosaminoglycan made of repeating disaccharide units (generally 2-9 units). Each glycosamine and iduronic acid residues (FIG. 1) are capable of multiple sulfation and acetylation patterns. Heparin interacts with numerous proteins. Direct attachment of heparin to the coating surface, which is commonly practiced in the art, would hinder the interaction between heparin and the various binding proteins. To maintain the anti-thrombogenic effect of heparin, the binding sites of heparin must be accessible to the binding protein. This can be achieved via a spacer.

The term "heparin" refers to a heparin molecule, a fragment of the heparin molecule, or a derivative of heparin. Heparin derivatives can be any functional or structural variation of heparin. Representative variations include alkali metal or alkaline—earth metal salts of heparin, such as sodium heparin (e.g., hepsal or pularin), potassium heparin (e.g., clarin), lithium heparin, calcium heparin (e.g., calciparine), magnesium heparin (e.g., cutheparine), and low molecular weight heparin (e.g., ardeparin sodium). Other examples include heparin sulfate, heparinoids, heparin based compounds and heparin having a hydrophobic counter-ion.

Heparin is a molecule which is very hydrophilic. It usually dissolves very well in water but not in organic solvent. This lack of solubility in organic solvents may limit the use of handling of heparin. Modification with a hydrophobic material may increase solubility of heparin in organic solvents and ease of handling heparin.

Useful hydrophobic materials for modifying heparin include hydrophobic polymers and hydrophobic counter ions. Heparin can be coupled or crosslinked to or grafted onto a hydrophobic polymer and complexed or conjugate to hydrophobic counter ions.

Any biocompatible polymers can be used to modify the hydrophilicity of heparin. Exemplary useful hydrophobic polymers include, but are not limited to, poly(ester amide), polystyrene-polyisobutylene-polystyrene block copolymer (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylene, polyfluoroalkylene, polyhydroxylkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly (ortho ester), polyphosphazenes, poly (phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly (vinylidene fluoride-co-chlorotrifluoroethylene) (PVDF-CTFE), poly(butyl methacrylate), poly(methyl methacrylate), poly(methacrylates), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(urea-urethanes) and a combination thereof. Methods of derivatizing heparin with hydrophobic materials or polymers are described in, for example, U.S. Pat. Nos. 4,331,697; 5,069,899; 5,236,570; 5,270,046; 5,453,171; 5,741,881; 5,770,563; 5,855,618; 6,589,943 and 6,630,580.

Any hydrophobic counter ions can be used to modify the hydrophilicity of heparin. For example, hydrophobic quaternary ammonium compounds have been commonly used to form complexes with heparin that are soluble in organic solvents. Some exemplary useful hydrophobic quaternary ammonium compounds and methods of forming complexes of these compounds with heparin are described in U.S. Pat. Nos. 4,654,327, 4,871,357 and 5,047,020.

Spacers

Generally, the spacers useful for attaching heparin and a polymer in a coating described herein have two functional groups, one capable of attaching to heparin, the other capable of attaching to the coating material. The spacer must have a grouping of atoms of such a length that the spacer, once attached to the heparin and then to the polymer, renders the heparin molecule flexible so as to allows a binding site of the heparin molecule to be accessible by a binding protein.

A general formula of the spacers can be Y—R—X where X and Y represent the two functional groups and R represents a monomeric, oligomeric, or polymeric di-radical.

Exemplary X and Y groups include, but are not limited to, hydroxyl, epoxide, carboxyl, amino, imide, aziridine, thiol, phosphoryl, aldehyde, anhydride, acyl halide, silyl, isocyanate, diisocyanate, carbodiimide, a dihydrazide, a multiaziridine, a multifunctional carbodiimide, a diamine, a primary amine side group on a polymer, N-hydroxy-succinamide, acryloxy terminated polyethylene glycol, methacryloxy terminated polyethylene glycol, and isothiocyanate.

Exemplary R di-radicals include hydrocarbon di-radicals, polyolefin di-radicals, polyether di-radicals, poly(alkylene glycol) di-radicals, poly(ethylene glycol) di-radicals, poly(ester amide) di-radicals, poly(ether amine) di-radicals, polyamino acid di-radicals, poly(hydroxy acid) di-radicals, polyhydroxyalkanoate di-radicals, polystyrene di-radicals, 2-methacryloyloxyethylphosphorylcholine (MPC), hydrophilic spacers, polyvinyl alcohol di-radicals, polyphosphazene di-radicals, poly(hydroxyl ethyl methacrylate) di-radicals, poly(hydroxyl ethyl acrylate) di-radicals, poly (hydroxyl propyl methacrylamide) di-radicals, hydroxyl propyl cellulose di-radicals, polyacrylic acid di-radicals, polyvinyl sulfonic acid di-radicals, polyalginate di-radicals, dextrin di-radicals, dextrose di-radicals, dextran di-radicals, carboxymethyl cellulose di-radicals, or hydroxyl functional poly(vinyl pyrrolidone) di-radicals.

The spacer can be provided by a linking agent comprising one of the di-radicals defined above or by a chemical agent comprising one of the di-radicals defined above.

Polymeric Substrate Surfaces

The heparin and modified heparin can be attached to any substrate surface. In one embodiment, the substrate surface can have a metallic surface modified with linking chemical agents such as silyl or siloxyl groups. The substrate surface can be made from a polymeric material. The substrate surface can be a polymeric coating with or without a bioactive agent.

In one embodiment of the present invention, the substrate surface is a polymeric coating surface formed of one or more polymeric material, in mixed blended or conjugated form. The coating may include one or more bioactive agent that can be a therapeutic agent. The polymeric material can be any biocompatible polymer such as a hydrophobic polymer, a hydrophilic polymer or a combination thereof.

The substrate can be made from or coated with a biostable or biodegradable polymer. "Biodegradable" refers to polymers that are capable of being completely degraded and/or eroded when exposed to bodily fluids such as blood and can be gradually resorbed, absorbed and/or eliminated by the body. The processes of breaking down and eventual absorption and elimination of the polymer can be caused by, for example, hydrolysis, metabolic processes, bulk or surface erosion, and the like. For coating applications, it is understood that after the process of degradation, erosion, absorption, and/or resorption has been completed, no polymer will remain on the device. In some embodiments, very negligible traces or residue may be left behind.

In one embodiment, the polymeric material is a hydrophobic polymer. Representative hydrophobic polymers include, but are not limited to, poly(ester amide), polystyrene-polyisobutylene-polystyrene block copolymer (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly (ortho ester), polyphosphazenes, poly (phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly (vinylidene fluoride-co-chlorotrifluoroethylene) (PVDF-CTFE), poly(butyl methacrylate), poly(methyl methacrylate), poly(methacrylates), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(2-hydroxyethyl methacrylate), PVDF-Solef® (polyvinylidenefluoride), poly(urea-urethanes) and a combination thereof. In some embodiments, the polymer can exclude any one of the aforementioned polymers.

In one embodiment, the polymeric material is a hydrophilic polymer. Representative hydrophilic polymers include, but are not limited to, polymers and co-polymers of hydroxyl ethyl methacrylate (HEMA), PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, alkoxymethacrylate, alkoxyacrylate, and 3-trimethylsilylpropyl methacrylate (TMSPMA), poly (ethylene glycol) (PEG), poly(propylene glycol), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), hydroxy functional poly(vinyl pyrrolidone), polyalkylene oxide, dextran, dextrin, sodium hyaluronate, hyaluronic acid, heparin, elastin, chitosan, and combinations thereof. In some embodiments, the polymer can exclude any one of the aforementioned polymers.

The composition described herein can be used for coating an implantable device such as a stent or for controlled delivery of a bioactive agent.

Method of Attaching Heparin to A Polymer or Polymeric Coating via A Spacer

The method of attaching heparin to a polymer or a polymeric coating can be achieved using a linking agent having at least two linking functionalities and a grouping that may serve as a spacer of the heparin. Optionally, heparin or a heparin/spacer species and a polymer can be functionalized to attach a reactive group to the carboxylic acid residue of heparin or to the spacer grouping of the heparin/spacer species and to the polymer. The heparin or heparin/spacer species are then coupled with each other via the linking agent (see, for example, Sorenson, W.; Sweeny, F.; Campbell, T., Preparative Methods of Polymer Chemistry, 3rd Edition, John Wiley & Sons, copyright 2001).

Useful functionalities that heparin or a heparin/spacer and a polymer can be functionalized to bear include, for example, hydroxyl, epoxide, carboxyl, amino, imide, aziridine, thiol, phosphoryl, aldehyde, anhydride, acyl halide, silyl, isocyanate, diisocyanate, carbodiimide, a dihydrazide, a multiaziridine, a multifunctional carbodiimide, a diamine, a primary amine side group on a polymer, N-hydroxysuccinamide, acryloxy terminated polyethylene glycol, methacryloxy terminated polyethylene glycol, and isothiocyanate.

Useful linking agents include, for example, agents bearing hydroxyl, epoxide, carboxyl, amino, imide, aziridine, thiol, phosphoryl, aldehyde, anhydride, acyl halide, silyl, isocyanate, diisocyanate, carbodiimide, a dihydrazide, a multiaziridine, a multifunctional carbodiimide, isothiocynate or a diamine functionalities, a polymer bearing a primary amine side group or side groups, N-hydroxy-succinamide, acryloxy terminated polyethylene glycol, and methacryloxy terminated polyethylene glycol. Other linking agents are listed in commercial catalogues such as Shearwater catalogue (Shearwater Polymers, Inc., Huntsville, Ala.) and Piercenet, found at www.Piercenet.com (Pierce Biotechnology, Inc., Rockford, Ill.).

The following describes a few embodiments of the present invention making a coating having heparin attached to a polymeric coating via a spacer.

Attachment Via Aldehyde

In one aspect of the present invention, a spacer can be coupled to heparin by reacting heparin possessing a terminal aldehyde to an amine terminated polymer as spacer such as PEG, as described in Scheme 2. The other end of the polymer can be a protected moiety that can form a functional group for grafting to a surface or coupling to a polymer using a carbodiimide such as 1-ethyl-3-(3-dimethylaminopropyl)-carbodiimide (EDC). The protected moiety can be, for example, a functionality capable of grafting to a surface or coupling to a polymer such as a carboxylic acid, amine, or hydroxyl group. An exemplary method of attaching PEG as a spacer to heparin is shown in Scheme 2 where an amine-terminated PEG is coupled to an aldehyde-terminated heparin, followed by removal of the t-BOC protective group on the second amine. The second amino can then be used to graft the heparin-spacer moiety to a polymer or a substrate surface.

Scheme 2

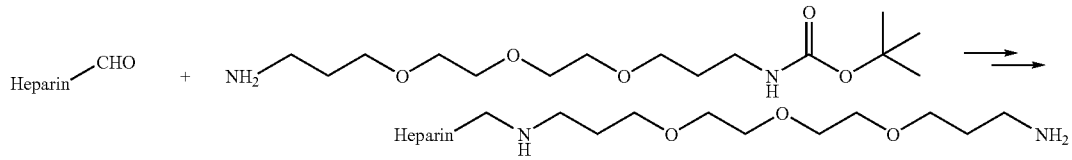

Heparin with a spacer can be attached to a polymeric substrate surface by direct coupling of the heparin/spacer species to a polymeric surface on a medical device via a functional group on the spacer distant from the heparin. Alternately, the heparin/spacer species can be first coupled to a polymer to form a heparin/spacer functionalized polymer, which can then be applied to a medical device to provide a non-thrombogenic surface on the medical device.

Attachment Via Carboxylic Acid

In one embodiment, a polymer having a carboxylic acid functionalized polymer backbone can be made. A heparin/spacer species can then be coupled to the polymer to form a conjugate having a general formula heparin-spacer-polymer. The heparin-spacer-polymer conjugate can be coated on a medical device. Alternately, a polymer having a carboxylic acid functionalized polymer backbone can be coated on a medical device to form a polymeric coating. The heparin-spacer species can then be grafted or coupled to the polymeric coating via a carboxyl functionality on the surface of the coating. For example, a hydrophobic copolymer of acrylic monomers such as methyl methacrylate (MMA) and t-butyl methacrylate (t-BMA) can be used as a coating with carboxyl functionalities. The carboxyl functionalities are obtained upon removal of the t-butyl protecting group. Scheme 3 shows the de-protection of an acrylic copolymer of MMA and t-BMA to yield a carboxylic acid bearing polymer.

Scheme 3

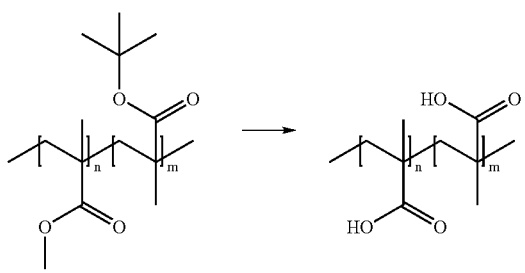

Alternately, a carboxyl containing monomer such as methacrylic acid or itaconic acid can be used to form a polymer bearing carboxyl functionalities. A functional group such as dihydrazide can be reacted to the carboxylic acid to give primary amine functionalities. Therefore, the polymer can be applied to a medical device to form a coating. A carboxy heparin/spacer species can be coupled to the carboxylic acid functionalities available at the surface, as depicted in Scheme 4 (upper path). This coupling can be mediated by, for example, a water soluble carbodiimide such as (1-ethyl-3-(3-(dimethylamino)propyl)carbodiimide (EDC). An alternative is to functionalize the heparin/spacer species and then graft the species onto the surface coated with the carboxylic acid functional polymer, as depicted in Scheme 4 (lower path).

Scheme 4

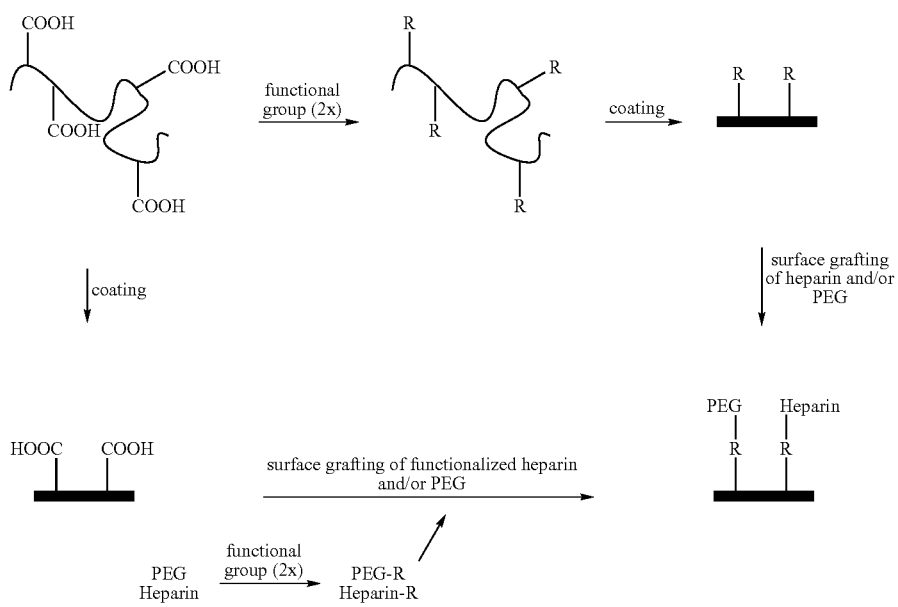

Amine terminated heparin/spacer species can be directly coupled to carboxylic acid moieties using an agent such as a carbodiimide such as EDC mediated by an agent such as N-hydroxybenzotriazole (HOBT), substituted HOBT, or N-hydroxysuccinamide. This can be done as grafting from the polymer coated surface, or as coupling to the copolymer that is subsequently applied to the surface to coat.

Attachment Via Hydrazide

In another aspect of the present invention, a heparin, which has a carboxylic acid moiety in its iduronic acid residue, can be coupled to a hydrazide reactive group in an aqueous medium such as water. A linking agent with at least two hydrazide reactive groups would be capable of coupling heparin with a coating surface having carboxylic acid groups. In order to avoid crosslinking of molecules bearing multiple carboxylic acid groups by the linking agent, the reaction is done in an excess of the linking agent such as a dihydrazide, and the degree of functionalization can be controlled by the amount of a carbodiimide such as EDC (Luo, Y. et al., J. Contr. Release 69:169-184 (2000)) (Scheme 5).

Scheme 5

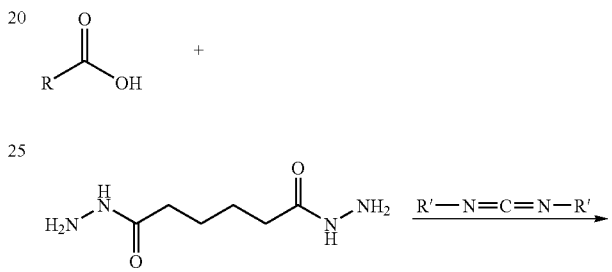

-continued

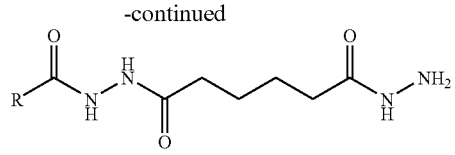

R = polymer or heparin

For example, an acrylic copolymer can be functionalized with a dihydrazide as shown in Scheme 6. The functionalized copolymer, which has a remaining hydrazide group,

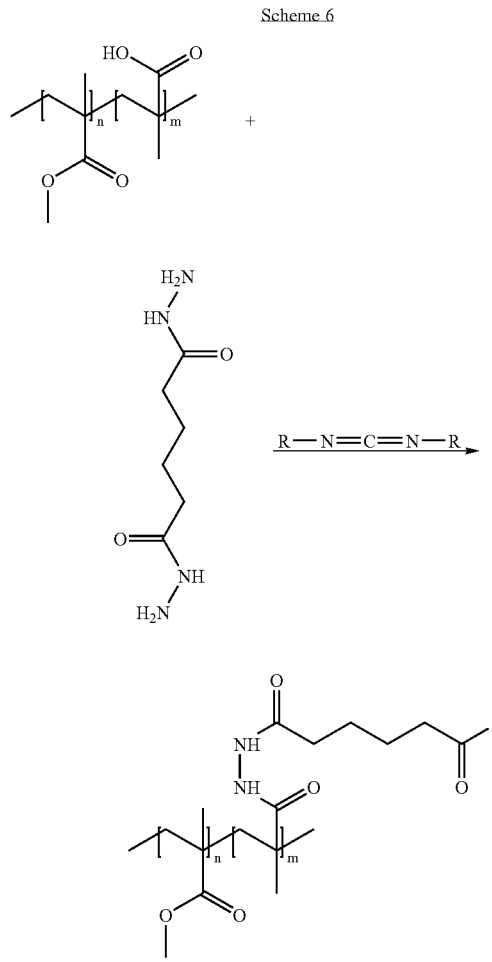

Scheme 6 can react with the carboxylic acid residue on heparin or a carboxylic end of the spacer part of the heparin/spacer conjugate using the carbodiimide chemistry and then can be coated on a medical device. Alternately, the functionalized copolymer can be coated onto a medical device, and heparin or a heparin/spacer conjugate then can be grafted onto the coating using the carbodiimide chemistry.

Attachment Via Multifunctional Aziridine

In accordance with a further aspect of the present invention, a multifunctional aziridine agent can be used as a crosslinker to couple a heparin or heparin/spacer conjugate with a polymer having carboxylic acid moieties. For example, pentaerythritol tris(3-aziridinopropionate) from Sybron Chemicals (NJ) can be used as a crosslinker (see, for example, Gianolino, D. A., et al., Crosslinked sodium hyaluronate containing labile linkages, Abstract from Society for Biomaterials 2002) (Scheme 7).

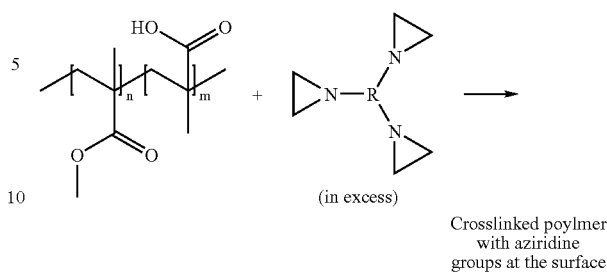

Scheme 7

(in excess)

Crosslinked poylmer with aziridine groups at the surface

The crosslinking of this polymer must be done on the surface to coat. By using an excess of the trifunctional crosslinker, some residual aziridine groups will still be available at the surface to graft heparin and optionally carboxy-PEG with or without spacer with a carboxylic acid functionality.

Multifunctional Carbodiimide

In another aspect of the present invention, a multifunctional carbodiimide can be used to attach heparin, with or without a spacer, to a polymer with carboxylic acid functionalities (see Scheme 8). Multifunctional carbodiimides are available from Nisshinbo (CARBODILITE™) and Bayer (BAYDERM™ Fix CD).

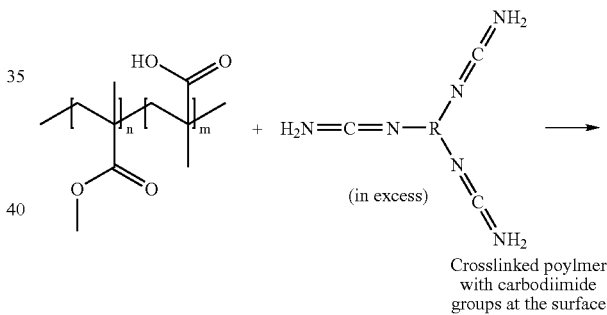

Scheme 8

(in excess)

Crosslinked poylmer with carbodiimide groups at the surface

Attachment to Polymers Formed of Primary Amine Functional Monomers

In accordance with a further aspect of the present invention, heparin, with or without a spacer, can be attached to a polymer formed of a monomer bearing primary amine functionalities via direct EDC mediated amide formation between the amine groups and the carboxyls on heparin and/or carboxy-PEG. Some examples of such a polymer is polyacrylic polymers formed of primary amine functional monomers such as N-(3-aminopropyl)methacrylamide HCl (available from Polysciences), ethyl 3-aminocrotonate (available from Aldrich), ethyl 3-amino-4,4,4-trifluorocrotonate (available from Aldrich), or combinations thereof. Succinimidyl derivatives of PEG can also react with these amino functional monomers in a facile manner. These monomers can polymerize with acrylates or methacrylates such as n-butyl methacrylate or methyl methacrylate. For example, as shown in Scheme 9, polymers substituted with mixed populations of PEG and heparin, with or without a spacer, can be produced via this scheme (Scheme 9).

Scheme 9

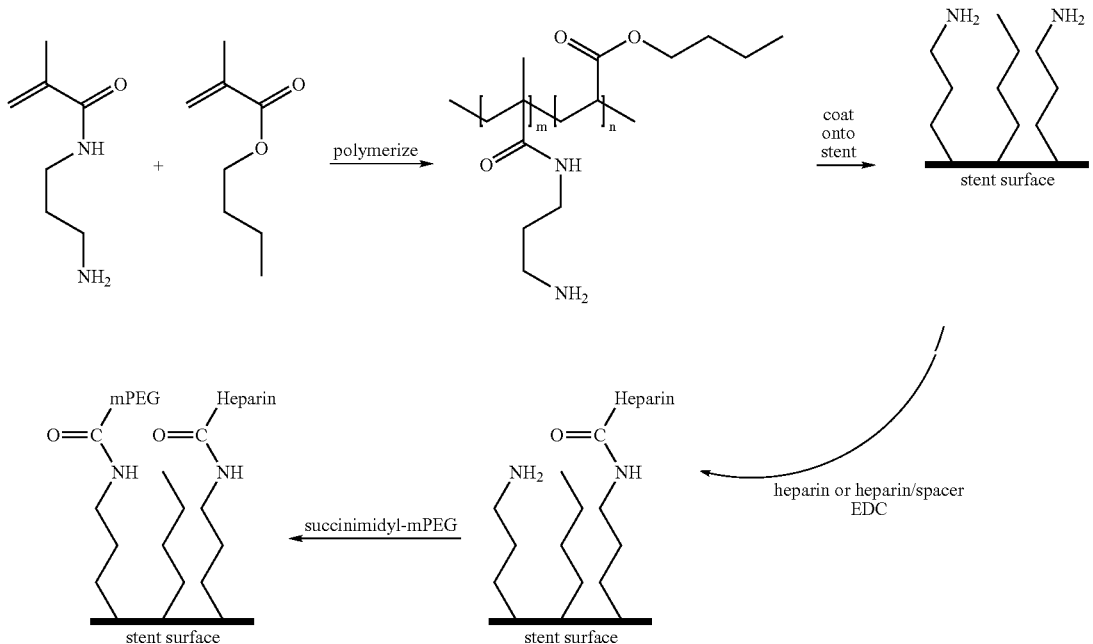

Succinimidyl derivatives of mPEG can be obtained from Nektar Corp. As an alternative, the entire polymer can be synthesized first, including heparin or the heparin/spacer species, optionally with PEG, and then applied to the stent.

Bioactive Agents

The polymeric coatings or the polymeric substrate described herein may optionally include one or more bioactive agents. The bioactive agent can be any agent which is biologically active, for example, a therapeutic, prophylactic, or diagnostic agent.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomagraphy (CT) and positron emission tomography (PET). Ultrasound diagnostic agents are typically a gas such as air, oxygen or perfluorocarbons.

In the case of controlled release, a wide range of different bioactive agents can be incorporated into a controlled release device. These include hydrophobic, hydrophilic, and high molecular weight macromolecules such as proteins. The bioactive compound can be incorporated into polymeric coating in a percent loading of between 0.01% and 70% by weight, more preferably between 5% and 50% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. The bioactive agent can also include any substance capable of exerting a therapeutic or prophylactic effect in the practice of the present invention. For example, the bioactive agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include alpha-interferon, genetically engineered epithelial cells, anti-inflammatory agents, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, cytostatic agents, prodrugs thereof, co-drugs thereof, and a combination thereof.

The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

Attachment of Heparin to a Methacrylate Copolymer

2-Ethoxyethyl methacrylate (10 g) and 2-ethylamino methacrylate hydrochloride (1 g) can be copolymerized by free radical polymerization in a solution of hexadecane and water (0.7 g and 80 g respectively) using tert-butylhydroperoxide (0.1 g) as a catalyst. After the addition of sodium formaldehyde sulfoxylate, the emulsion can be let to react for 60 min. at 60° C. The resulting polymer can be precipitated in cold methanol.

The methacrylic copolymer (2 g) can be dissolved with heparin aldehyde (0.4 g) in dimethyl formamide (10 wt % solids). Sodium cyanoborohydride can be added to the solution, which can be stirred for 48 h at 40° C. The resulting polymer can be precipitated in water, filtered and dried under vacuum for 48 h.

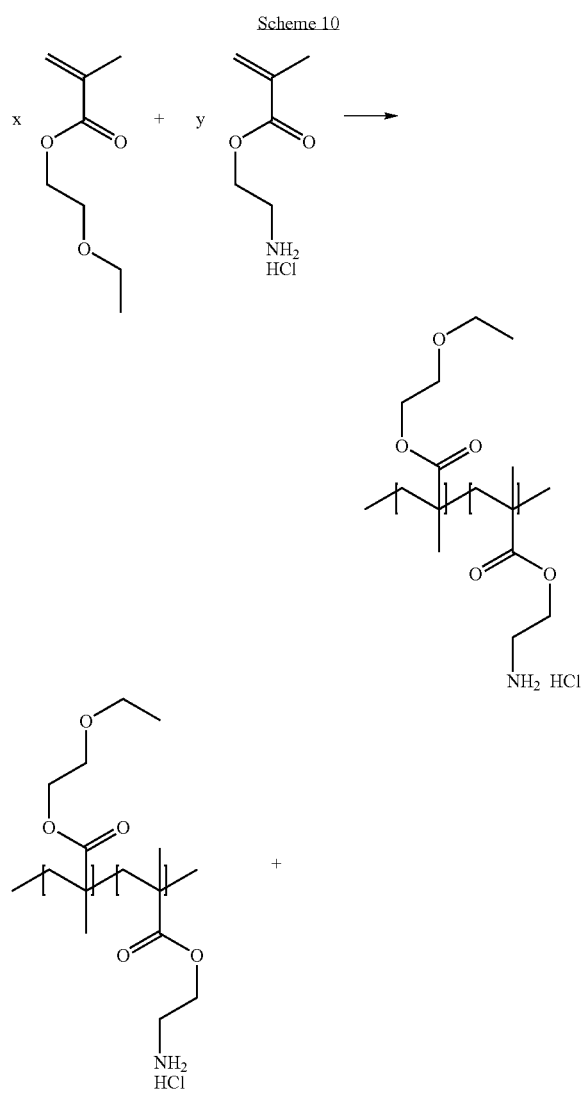

Scheme 10

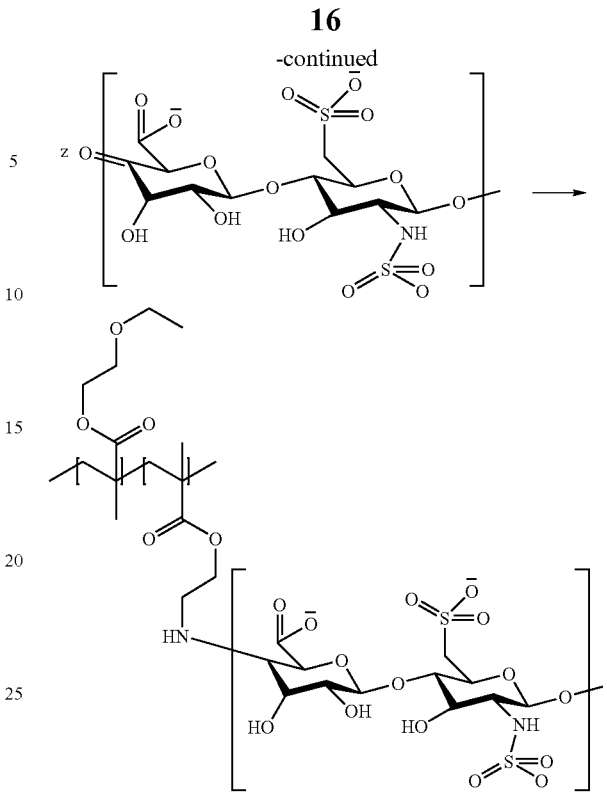

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device comprising a substrate and a polymeric coating which comprises a biocompatible polymer and heparin,
   wherein heparin is attached to the biocompatible polymer via a spacer having a grouping that renders a binding site of the heparin molecule accessible by a binding protein,
   wherein the spacer is of a formula of Y-R-X where X and Y represent two functional groups and R represents a monomeric di-radical;
   wherein X and Y groups are independently selected from the group consisting of hydroxyl, epoxide, carboxyl, amino, imide, aziridine, thiol, phosphoryl, aldehyde, anhydride, acyl halide, silyl, isocyanate, di-isocyanate, carbodiimide, a dihydrazide, a multiaziridine, a multi-functional carbodiimide, a diamine, N-hydroxy-succinamide, acryloxy terminated polyethylene, glycol, methacryloxy terminated polyethylene glycol, and isothiocyanate; and
   R is a dextrose di-radical; and
   wherein heparin is molecular heparin, a fragment of heparin, or a derivative thereof.

2. The medical device of claim 1 wherein the heparin is a heparin bearing a hydrophobic counter ion or a hydrophobic material.

3. The medical device of claim 2, wherein the polymeric coating further comprises a bioactive agent.

4. The medical device of claim 1 wherein the biocompatible polymer is selected from the group consisting of poly (ester amides), polycaprolactone (PCL), poly(L-lactide), poly(D,L-lactide), poly(lactides), polylactic acid (PLA), poly(lactide-co-glycolide), poly(glycolide), and combinations thereof.

5. The medical device of claim 4, wherein the polymeric coating further comprises a bioactive agent.

6. The medical device of claim 1, wherein the polymeric coating further comprises a bioactive agent.

7. The medical device of claim 6 wherein the bioactive agent is selected from the group consisting of paclitaxel, docetaxel, estradiol, nitric oxide donors, super oxide dismutases, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy] ethyl-rapamycin, 40-O-tetrazole-rapamycin, ABT-578, clobetasol, and combinations thereof.

8. The medical device of claim 6 wherein the bioactive agent is selected from the group consisting of antiproliferative, antineoplastic, anti-inflammatory, steroidal anti-inflammatory, non-steroidal anti-inflammatory, antiplatelet, anticoagulant, antifibrin, antithrombin, antimitotic, antibiotic, antiallergic, and antioxidant substances, cytostatic agents, and combinations thereof.

9. A method of treating a disorder in a human being by implanting in the human being the medical device as defined in claim 6,
wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

10. A method of treating a disorder in a human being by implanting in the human being the medical device as defined in claim 1,
wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

11. The medical device of claim 1, wherein the biocompatible polymer is selected from the group consisting of poly(ester amides), polystyrene-polyisobutylene-polystyrene block copolymers (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylenes, polyhydroxyalkanoates, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hydroxyhexanoate), poly(trimethylene carbonate), poly(ortho esters), polyphosphazenes, poly(phosphoesters), poly(tyrosine derived arylates), poly(tyrosine derived carbonates), polydimethyloxanone (PDMS), poly- dimethylsiloxane, poly(butyl methacrylate), poly(methyl methacrylate) (PMMA), poly(meth- acrylates), poly(vinyl acetate), poly (ethylene-co-vinyl acetate), poly(ethylene-co-vinyl alcohol), poly(ester urethanes), poly(ether-urethanes), poly(carbonate-urethanes), poly(silicone-urethanes), poly(2-hydroxyethyl methacrylate), poly(urea-urethanes), polymers and copolymers of PEG acrylate (PEGA), PEG methacrylate, 2-methacryloyloxyethylphosphorylcholine (MPC), and/or n-vinyl pyrrolidone (VP); polymers and copolymers of carboxylic acid bearing monomers; polymers and copolymers formed of methacrylic acid (MA), and/or acrylic acid (AA); polymers and copolymers formed of hydroxyl bearing monomers; polymers and copolymers formed of hydroxyl ethyl methacrylate (HEMA), hydroxypropyl methacrylate (HPMA), hydroxypropylmethacrylamide, 3-trimethylsilylpropyl methacrylate (TMSPMA), alkoxymethacrylate, and/or alkoxyacrylate; poly(ethylene glycol)(PEG), poly(propylene glycol), SIS-PEG, polystyrene-PEG, polyisobutylene-PEG, PCL-PEG, PLA-PEG, PMMA-PEG, PDMS- PEG, polypropylene oxide-co-polyethylene glycol surfactants, poly(tetramethylene glycol), hydroxy functional poly(vinyl pyrrolidone), polyalkylene oxides, dextran, dextrin, sodium hyaluronate, hyaluronic acid, elastin, chitosan, and combinations thereof.

12. A polymeric composition comprising a biocompatible polymer and heparin,
wherein heparin is attached to the biocompatible polymer via a spacer having a grouping that renders a binding site of the heparin molecule accessible by a binding protein,
wherein the spacer has a formula of Y—R—X where X and Y represent two functional groups and R represents a monomeric di-radical;
wherein X and Y groups are independently selected from the group consisting of hydroxyl, epoxide, carboxyl, amino, imide, aziridine, thiol, phosphoryl, aldehyde, anhydride, acyl halide, silyl, isooyanate, di-isocyanate, carbodiimide, a dihydrazide, a multiaziridine, a multi-functional carbodiimide, a diamine, a primary amine side group on a polymer, N-hydroxy- succinamide, acryloxy terminated polyethylene glycol, methacryioxy terminated polyethylene glycol, and isothiocyanate; and
R is a dextrose di-radical; and
wherein heparin is molecular heparin, a fragment of heparin, or a derivative thereof.

13. The polymeric composition of claim 12 wherein the heparin is a heparin bearing a hydrophobic counter ion or a hydrophobic material.

14. The polymeric composition of claim 13 further comprising a bioactive agent.

15. The polymeric composition of claim 12, wherein the biocompatible polymer is selected from the group consisting of poly(ester amides), polycaprolactone (PCL), poly(L-lactide), poly(D,L-lactide), poly(lactides), polylactic acid (PLA), poly(lactide-co-glycolide), poly(glycolide), and combinations thereof.

16. The polymeric composition of claim 15 further comprising a bioactive agent.

17. The polymeric composition of claim 12 further comprising a bioactive agent.

18. The polymeric composition of claim 17 wherein the bioactive agent is selected from the group consisting of paclitaxel, docetaxel, estradiol, nitric oxide donors, super oxide dismutases, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy) ethoxy]ethyl-rapamycin, 40-O-tetrazole-rapamycin, ABT-578, clobetasol, and combinations thereof.

19. The polymeric composition of claim 17, wherein the bioactive agent is selected from the group consisting of antiproliferative, antineoplastic, anti-inflammatory, steroidal anti-inflammatory, non-steroidal anti-inflammatory, antiplatelet, anticoagulant, antifibrin, antithrombin, antimitotic, antibiotic, antiallergic, and antioxidant substances, cytostatic agents, and combinations thereof.

20. The polymeric composition of claim 12, wherein the biocompatible polymer is selected from the group consisting of poly(ester amides), polystyrene- polyisobutylene-polystyrene, block copolymers (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylenes, polyhydroxyalkanoates, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hydroxyhexanoate), poly(trimethylene carbonate), poly(ortho esters), polyphosphazenes, poly(phosphoesters), poly(tyrosine derived arylates), poly(tyrosine derived carbonates), polydimethyloxanone (PDMS), polydimethylsiloxane, poly(butyl methacrylate), poly(methyl methacrylate) (PMMA), poly(methacrylates), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(2-hydroxyethyl methacrylate), poly(urea-urethanes), polymers and copolymers of PEG acrylate (PEGA), PEG methacrylate, 2-methacryloyloxyethylphosphorylcholine (MPC), and/or n-vinyl pyrrolidone (VP); polymers and copolymers of carboxylic acid bearing monomers; polymers and copolymers formed of methacrylic add (MA), and/or acrylic add (AA); polymers and copolymers formed of hydroxyl bearing monomers; polymers and copolymers formed of hydroxyl ethyl methacrylate (HEMA), hydroxypropyl methacrylate (HPMA), hydroxypropylmethacrylamide, 3-trimethylsilylpropyl methacrylate (TMSPMA), alkoxymethacrylate, and/or alkoxyacrylate; poly(ethylene glycol)(PEG), poly(propylene glycol), SIS-PEG, polystyrene-PEG, polyisobutylene-PEG, PCL-PEG, PLA-PEG, PMMA-PEG, PDMS- PEG, polypropylene oxide-co-polyethylene glycol surfactants, poly(tetramethylene glycol), hydroxy functional poly(vinyl pyrrolidone), polyalkylene oxides, dextran, dextrin, sodium hyaluronate, hyaluronic add, elastin, chitosan, and combinations thereof.

21. A method of making a polymeric composition comprising a biocompatible polymer and heparin, comprising:
providing a biocompatible polymer which is optionally functionalized,
providing heparin which is optionally functionalized, and coupling heparin to the biocompatibie polymer via a spacer having a grouping that renders a binding site of the heparin molecule accessible by a binding protein,
wherein the spacer is of a formula of Y—R—X where X and Y represent two functional groups and R represents a monomeric di-radical;
wherein X and Y groups are independently selected from the group consisting of hydroxyl, epoxide, carboxyl, amino, imide, aziridine, thiol, phosphoryl, aldehyde, anhydride, acyl halide, silyl, isocyanate, di-isocyanate, carbodiimide, a dihydrazide, a multiaziridine, a multifunctional carbodiimide, a diamine, N-hydroxy-succinamide, acryloxy terminated polyethylene glycol, methacryloxy terminated polyethylene glycol, and isothiocyanate; and
R is a dextrose di-radical; and
wherein heparin is molecular heparin, a fragment of heparin, or a derivative thereof.

22. The method of claim 21 wherein the heparin is a heparin bearing a hydrophobic counter ion or a hydrophobic material.

23. The method of claim 21 wherein the biocompatible polymer is selected from the group consisting of polyester amides), polystyrene-polyisobutylene-polystyrene block copolymers (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylenes, polyhydroxyalkanoates, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hydroxyhexanoate), poly(trimethylene carbonate), poly(ortho esters), polyphosphazenes, poly(phosphoesters), poly(tyrosine, derived arylates), poly(tyrosine derived carbonates), polydimethyloxanone (PDMS), polydimethylsiloxane, poly(butyl methacrylate), poly(methyl methacrylate) (PMMA), poly(methacrylates), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(2-hydroxyethyl methacrylate), poly(urea-urethanes), polymers and copolymers of PEG acrylate (PEGA), PEG methacrylate, 2-methacryloyloxyethylphosphorylcholine (MPC) and/or n-vinyl pyrrolidone (VP); polymers and copolymers of carboxylic acid bearing monomers; polymers and copolymers formed of methacrylic acid (MA), and/or acrylic acid (AA); polymers or copolymers formed of hydroxyl bearing monomers; polymers or copolymers formed of hydroxy ethyl methacrylate (HEMA), hydroxypropl methacrylate (HPMA), hydroxypropylmethacrylamide, 3- trimethylsilylpropyl methacrylate (TMSPMA), alkoxymethacrylate, and/or alkoxyacrylate; poly(ethylene glycol)(PEG), poly(propylene glycol), SIS-PEG, polystyrene-PEG, polyisobutylene-PEG, PCL-PEG, PLA-PEG, PMMA-PEG, PDMS-PEG, polypropylene oxide-co-polyethylene glycol surfactants, poly(tetramethylene glycol), hydroxy functional poly(vinyl pyrrolidone), polyalkylene oxides,-dextran, dextrin, sodium hyaluronate, hyaluronic acid, elastin, chitosan, and combinations thereof.

* * * * *